(12) United States Patent
Buschmann et al.

(10) Patent No.: US 11,751,980 B2
(45) Date of Patent: Sep. 12, 2023

(54) ABUTMENT WITH EMBEDDED SCREW

(71) Applicant: STRAUMANN HOLDING AG, Basel (CH)

(72) Inventors: Daniel Buschmann, Kaiseraugst (CH); Philippe Chavanne, Liestal (CH); Jasmine Rüegg, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 284 days.

(21) Appl. No.: 17/257,622

(22) PCT Filed: Jun. 19, 2019

(86) PCT No.: PCT/EP2019/066259
§ 371 (c)(1),
(2) Date: Jan. 4, 2021

(87) PCT Pub. No.: WO2020/007616
PCT Pub. Date: Jan. 9, 2020

(65) Prior Publication Data
US 2021/0137650 A1 May 13, 2021

(30) Foreign Application Priority Data
Jul. 4, 2018 (EP) .................................... 18181719

(51) Int. Cl.
*A61C 8/00* (2006.01)
*B33Y 50/02* (2015.01)
(Continued)

(52) U.S. Cl.
CPC .......... *A61C 8/0069* (2013.01); *A61C 8/0012* (2013.01); *A61C 13/0019* (2013.01);
(Continued)

(58) Field of Classification Search
CPC . A61C 8/0069; A61C 8/0012; A61C 13/0019; B33Y 50/02; B33Y 80/00;
(Continued)

(56) References Cited

U.S. PATENT DOCUMENTS

2014/0046384 A1\* 2/2014 Horwitz ............... A61B 17/864
606/304
2014/0178836 A1 6/2014 Haus et al.
(Continued)

FOREIGN PATENT DOCUMENTS

DE 20 2012 102 746 U1 8/2012

OTHER PUBLICATIONS

Sep. 19, 2019 International Search Report issued in International Patent Application No. PCT/EP2019/066259.

*Primary Examiner* — Thomas C Lee
*Assistant Examiner* — Ameir Myers
(74) *Attorney, Agent, or Firm* — Oliff PLC (57) ABSTRACT

A dental abutment system including an abutment, an inlay and screw, wherein the screw at least partially occupies the interior channel of the inlay. A method of manufacturing a dental abutment system and to a control data set including a plurality of control instructions that are configured to, when implemented in an additive manufacturing system, to cause the system to execute at least the step of forming an abutment at the distal end of an inlay using an additive manufacturing process. The screw is a captive screw. The interior channel of the abutment is variable in diameter and the smallest diameter is ≥102% and ≤110% of the width of the screw head and the longitudinal axis of the interior channel of the abutment and the longitudinal axis of the interior channel of the inlay are angled with respect to each other at an angle of ≥5 degrees.

20 Claims, 7 Drawing Sheets

(51) Int. Cl.
  *B22F 10/85*    (2021.01)
  *B33Y 80/00*    (2015.01)
  *B29C 64/393*   (2017.01)
  *G16H 20/40*    (2018.01)
  *A61C 13/00*    (2006.01)
  *G05B 19/4099*  (2006.01)

(52) U.S. Cl.
  CPC ............ *B22F 10/85* (2021.01); *B29C 64/393* (2017.08); *B33Y 50/02* (2014.12); *B33Y 80/00* (2014.12); *G05B 19/4099* (2013.01); *G16H 20/40* (2018.01); *G05B 2219/45167* (2013.01)

(58) Field of Classification Search
  CPC ....... B29C 64/393; G16H 20/40; B22F 10/85; G05B 19/4099; G05B 2219/45167
  See application file for complete search history.

(56) References Cited

U.S. PATENT DOCUMENTS

| | | |
|---|---|---|
| 2016/0062346 A1 | 3/2016 | Akmakjian |
| 2016/0206408 A1* | 7/2016 | Spindler .............. A61C 8/0077 |
| 2017/0056134 A1* | 3/2017 | Cordonnier ........ A61C 13/0022 |
| 2020/0093578 A1* | 3/2020 | Spindler ................ A61C 8/006 |
| 2020/0289243 A1* | 9/2020 | Jinton ................ A61C 13/0022 |

* cited by examiner

FIG. 5 (comparative example)

FIG. 6 (comparative example)

ABUTMENT WITH EMBEDDED SCREW

The present invention relates to a dental abutment system comprising an abutment including an interior channel of variable diameter, an inlay and a screw, wherein the screw at least partially occupies the interior channel of the inlay. The invention also relates to a method of manufacturing such a dental abutment system and to a control data set comprising a plurality of control instructions, wherein the control instructions are configured to, when implemented in an additive manufacturing system, to cause the system to execute at least the step of forming an abutment at the distal end of an inlay using an additive manufacturing process.

Dental implants are used to replace individual teeth or for anchoring more complex structures, which generally replace several or even all of the teeth. The materials used for dental implants are often titanium and alloys thereof. These materials have the necessary strength for withstanding the mechanical loads that occur, and they are at the same time sufficiently biocompatible for osseointegration and long term use in the mouth.

Implants have two essential parts: an anchoring part and an abutment part. The anchoring part is embedded in the bone, where it osseointegrates with the bone tissue to provide a firm anchor for the prosthesis. The abutment extends into the oral cavity and provides a support for the prosthesis. The desired prosthetic element (e.g. bridge or crown) is fastened over the abutment such that at least part of the abutment is housed within the prosthesis and provides core support to this. The prosthetic element can be adhesively bonded, cemented, screwed or directly veneered onto the abutment.

The implant can be constructed in one part, such that the anchoring part and abutment part are produced in one integral piece. Hence in such implant systems the integrated anchoring part and abutment are always positioned within the mouth at the same time and the single piece implant extends through the soft tissue into the oral cavity to form a core support for the prosthesis.

However, implants are also often constructed in two or more parts, in which case they consist of at least an anchoring component, often referred to in isolation as the implant, and a separate abutment, sometimes referred to as a spacer. The anchoring component is usually either embedded completely in the bone, that is to say to the height of the alveolar crest, or protrudes by a few millimeters from the alveolar crest into the soft tissue. The abutment is mounted either directly or indirectly to the anchoring component after the latter has become incorporated (osseointegrated) into the bone or directly after the anchoring component has been inserted. It can also be attached to the anchoring component prior to insertion. Most usually the abutment is not mounted until after osseointegration. In such cases a component called a healing cap is often mounted to the implant during the osseointegration process to prevent incursion of soft tissue over the implant site.

In contrast to one piece implants, multi-part implants are more versatile, because the anchoring part and the abutment can be adapted to individual requirements. In particular, the abutment shape and angulation, relative to the anchoring part, can be selected after implant insertion. This provides the surgeon with more flexibility and room for error in the placement of the implant. An additional advantage of multi-part implants is that the abutment can be made from a different material than the anchoring part.

When the abutment is fastened to the implant, possibly with an intermediate inlay, the fastening screw can simply be inserted vertically into the assembly. Alternatively, an angulated screw channel can be used. However, this conventional approach has its own drawbacks due to the need of widening the screw channel in order to allow the screw to be inserted through the abutment prior to fastening the abutment to the implant. If the screw hole in the upper part of the abutment is bigger some post processes are needed to close that hole afterwards. The challenge is to close the hole without visible tracks and to guarantee the stability of an abutment with a "normal" hole. At the moment the problem is addressed with conventional methods which waive the need for a screwed crown and use a cemented crown instead.

With the common method to close these screw channel holes the stability of the abutment is not as good as the stability of an abutment with a "normal", vertical screw channel orientation. As well, the esthetic is not as smooth as the abutment with a hidden screw channel hole (which is possible with an angulated screw channel).

WO 2015/049149 A1 discloses a dental kit-of-parts comprising an implant abutment, a dental restoration and a screw. The head of the screw is provided in a recess formed in the kit-of-parts, with the screw shaft extending through a hole in the implant abutment. A channel in the dental restoration allows access to the screw head by a tool, wherein the diameter of the channel is smaller than the diameter of the screw head. The dental kit-of parts can be manufactured using rapid prototyping such that the captive screw is formed within the combination of the implant abutment and the dental restoration or through conventional means, with the dental abutment and the dental restoration being ex-situ connected to enclose the screw.

The present invention has the object of providing a dental abutment system with enhanced mechanical stability, lower material costs, increased production speed and more user-friendly venerability around the screw channel aperture. This object has been achieved by a dental abutment system according to claim 1, a method of manufacturing a dental abutment system according to claim 13 and a control data set according to claim 18. Advantageous embodiments are the subject of the dependent claims. They may be combined freely unless the context clearly indicates otherwise.

Accordingly, a dental abutment system comprises an abutment, an inlay and a screw, wherein the system has a proximal end and a distal end, the abutment being at the distal end and the inlay at the proximal end of the system. The abutment comprises an interior channel having a longitudinal axis and the inlay comprises an interior channel having a longitudinal axis. The abutment and the inlay are positioned relative to each other in such a way that the interior channel of the abutment at least partially extends into the interior channel of the inlay. The abutment and the inlay are at least partially fused to each other. The screw has a proximal end and a distal end, the distal end comprising a screw head and the proximal end comprising a thread for engaging with a bone implant and the screw at least partially occupies the interior channel of the inlay.

The diameter of the interior channel of the abutment varies from the distal to the proximal end and the smallest diameter is ≥102% and ≤110% of the width of the screw head and the longitudinal axis of the interior channel of the abutment and the longitudinal axis of the interior channel of the inlay are angled with respect to each other at an angle of ≥5 degrees (preferably ≥20 degrees to ≤35 degrees, more preferred ≥22 degrees to ≤25 degrees).

In a system according to the invention it is possible to minimize the hole in the upper part of the abutment with an angulated screw channel. This is due to the fact that the screw can be regarded as a captive screw. If the screw is already in the channel of the inlay during the production of the abutment, the channel in the abutment (which is needed to access the screw with a tool for fastening the abutment system to an implant) can get thinner and as a conclusion, the hole in the abutment can be minimized. Furthermore, based on the variable diameter of the interior channel it is possible to use less material compared to solutions comprising a uniform and small interior channel diameter. In addition, it is possible to provide more guidance to the screw and, based on the position of the smaller diameter, it is possible to provide more mechanical strength in these channel regions. Therefore, it is possible to adapt the mechanical properties of the abutment in a wide range. Such solution is superior compared to state of the art solutions using only a single and large inner diameter.

By way of example, the abutment may be 3D-printed on top of an inlay into whose channel the screw has already been inserted. If the screw extends out of the upper part of the inlay the abutment can be 3D-printed around the screw as well. It is also possible to insert a semi-finished screw and 3D-print the screw head during the same manufacturing process. Other methods of fabrication include casting the abutment onto the inlay with a flexible spacer to define the channels which will be removed after the casting. Furthermore, it is possible to insert the screw after forming the abutment.

The abutment may be patient-specific, which is especially easy to realize in 3D-printing. This technique of producing a patient specific abutment with an angulated screw channel can also be applied to a whole bridge.

With respect to the method according to the invention, a method of manufacturing a dental abutment system comprises the steps of:
A) providing an inlay,
  the inlay having a proximal and a distal end and comprising an interior channel having a longitudinal axis proximaldistal;
B) providing a screw, the screw having a proximal end and a distal end,
  the distal end of the screw comprising at least a part of or an entire screw head and the proximal end comprising a thread for engaging with a bone implant;
C) forming an abutment at the distal end of the inlay using an additive manufacturing process, thereby at least partially fusing the formed abutment to the inlay,
  the abutment comprising an interior channel having a longitudinal axis,
  wherein the abutment and the inlay are positioned relative to each other in such a way that the interior channel of the abutment at least partially extends into the interior channel of the inlay.

Step C) is performed in such a manner that the diameter of the interior channel of the abutment varies from the distal to the proximal end and the smallest diameter of the interior channel of the abutment is ≥102% and ≤110% (preferably ≥103% to ≤108%) of the width of the screw head and that the longitudinal axis of the interior channel of the abutment and the longitudinal axis of the interior channel of the inlay are angled with respect to each other at an angle of ≥5 degrees (preferably ≥20 degrees to ≤35 degrees, more preferred ≥22 degrees to ≤25 degrees). The proximal end of the screw channel is preferably straight in its initial stage to allow the screw to fully retreat into the finished abutment before the angulation starts.

In the method according to the invention the inlay serves as the build platform for the abutment. As the screw can for instance already in place a captive screw configuration can be achieved. It is preferred that at least the abutment and the inlay are manufactured from the same material.

The screw which is provided in step B) comprises, on its distal end, at least a part of a screw head or an entire screw head. In one embodiment of the method the screw provided in step B) comprises, on its distal end, a partial screw head and during the forming of the abutment in step C) the screw head is simultaneously finished using the same additive manufacturing process for forming the abutment.

In another embodiment of the method step A) and/or step B) are performed as an additive manufacturing step.

In another embodiment of the method step A) and step B) are performed as a simultaneous additive manufacturing step. This is especially feasible in powder-based processes where non-fused powder particles can act as a temporary support for the build intermediates. The inlay and screw would be manufactured in such a way that the screw is already in position within the channel of the inlay. Non-fused powder can then be expelled through the channels of the finished abutment system.

In another embodiment of the method the additive manufacturing step or steps employ a metal powder, a ceramic powder or a polymer powder as their build material. The abutment, the inlay and/or the screw may be constructed from titanium, cobalt-chromium alloy, aluminum oxide, zirconium oxide or hydroxyl apatite. Titanium and CoCr alloy can be processed in selective laser sintering (SLS), selective laser melting (SLM) additive manufacturing techniques or direct energy deposition (DED) e.g. Laser Cladding. Aluminum oxide, zirconium oxide and hydroxyl apatite can be processed in binder and/or material jetting additive manufacturing techniques.

In another embodiment of the method, in step C) the abutment is formed according to spatial data of an individual person. The spatial data can be obtained from an intra-oral scanning image. Such individualization of the abutment leverages the advantages of 3D-printing techniques.

With respect to the data set according to the invention, a control data set comprises a plurality of control instructions, wherein the control instructions are configured to, when implemented in an additive manufacturing system, to cause the system to execute at least the step of:
  forming an abutment at the distal end of an inlay using an additive manufacturing process,
    the abutment comprising an interior channel having a longitudinal axis,
    the inlay having a proximal and a distal end and comprising an interior channel having a longitudinal axis;
    a screw, the screw having a proximal end and a distal end,
      the distal end of the screw comprising a screw head and the proximal end comprising a thread for engaging with a bone implant;
    wherein the abutment and the inlay are positioned relative to each other in such a way that the interior channel of the abutment at least partially extends into the interior channel of the inlay.

The forming of the abutment is performed in such a manner that the diameter of the interior channel of the abutment varies from the distal to the proximal end and the smallest diameter of the interior channel of the abutment is ≥102% and ≤110% (preferably ≥103% to ≤108%) of the width of the screw head and that the longitudinal axis of the interior channel of the abutment and the longitudinal axis of the interior channel of the inlay are angled with respect to each other at an angle of ≥5 degrees (preferably ≥20 degrees to ≤35 degrees, more preferred ≥22 degrees to ≤25 degrees). Therefore, it is possible that the data set includes control instructions, wherein the screw is processed within the interior channel of the abutment at the same time as the abutment system. It is also possible that the data set includes control instructions, wherein the screw is processed outside and/or after processing the interior channel. In the case that the screw is processed with the abutment in a one-step routine, the smallest diameter of the interior channel of the abutment can be ≥80% and ≤110% (preferably ≥90% to ≤105%).

In an embodiment of the data set the control instructions are further configured to cause the additive manufacturing system to execute, prior to the forming of the abutment, the step of:

simultaneously forming an inlay and a screw,
the inlay having a proximal and a distal end and comprising an interior channel having a longitudinal axis;
a screw being at least partially located within the interior channel of the inlay, the screw having a proximal end and a distal end,
the distal end of the screw being located at the distal end of the inlay,
the distal end of the screw comprising a screw head and the proximal end comprising a thread for engaging with a bone implant.

In another embodiment of the data set it comprises data for forming the abutment which correspond to spatial data of an individual person.

The present invention will be further described with reference to the following figures without wishing to be limited by them.

FIG. 1 shows components of a dental abutment system according to the invention. Depicted are an abutment 10, an inlay 20 and a screw 30. As indicated in the figure, the system has a proximal and a distal end. As such, when implemented in the mandible of a patient, the proximal end of the system will face the jaw bone. In the system according to the invention the abutment is 10 located at the distal end and the inlay 20 at the proximal end.

Figure 1:
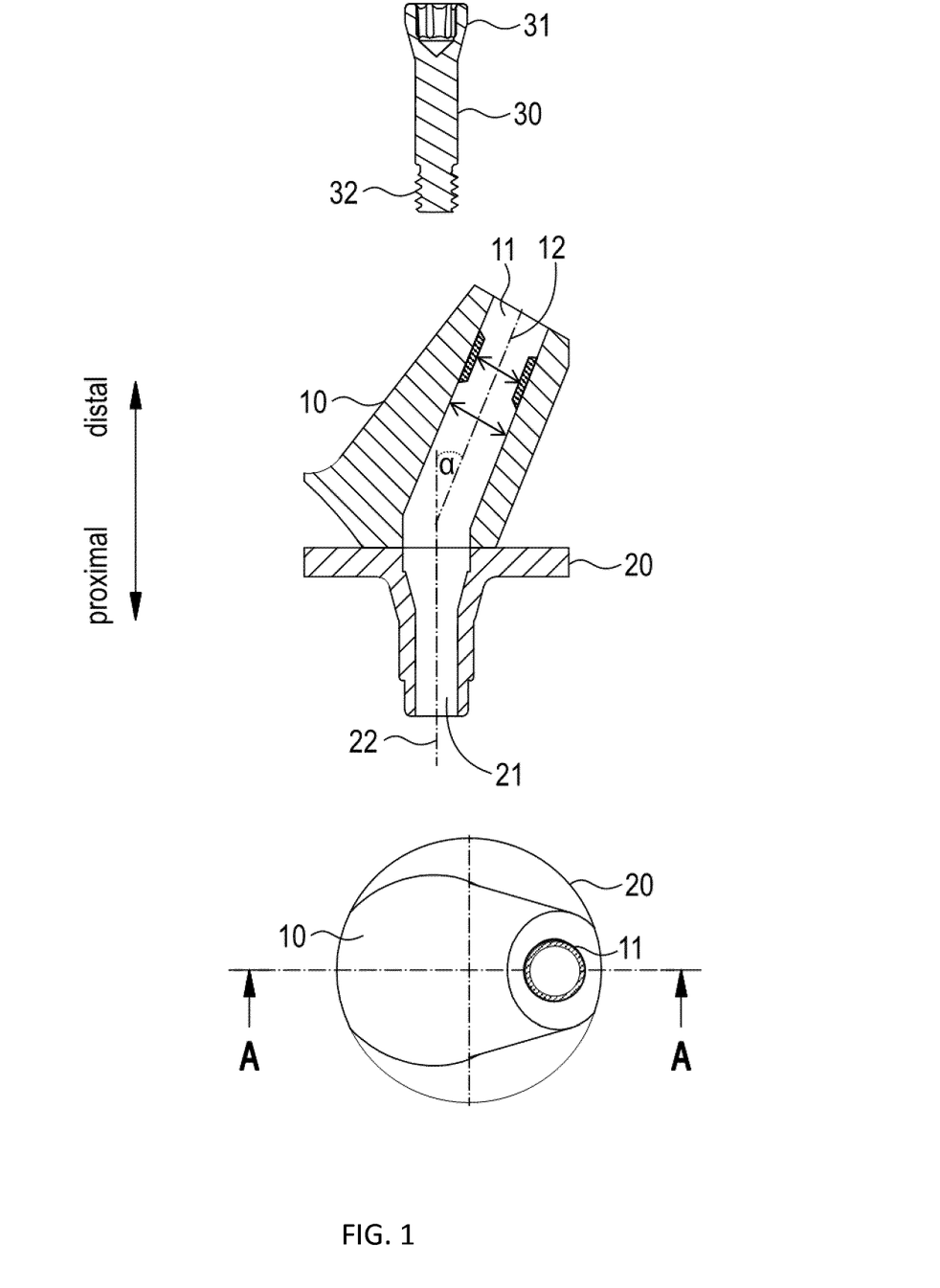
FIG. 1 shows components of a dental abutment system according to the invention

The abutment 10 comprises an interior channel 11 having a longitudinal axis 12 and the inlay 20 comprises an interior channel 21 having a longitudinal axis 22. By way of definition, the axes 12 and 22 are the axes along which the channels 11 and 21 extend the most. This distinction can be seen in FIG. 1a where the channel 11 has a bend and the longitudinal axis after the bend is identical to the longitudinal axis 22.

Furthermore, the abutment 10 and the inlay 20 are positioned relative to each other in such a way that the interior channel 11 of the abutment 10 at least partially extends into the interior channel 21 of the inlay 20. It is preferred that these channels fully extend into each other. A partial extension would implicate that a constriction exists between the two channels which is generally less desirable. In a full extension, as shown here, the channels have the same diameter at the interface of the abutment 10 and the inlay 20 and their cross-sections are superimposed upon each other. In addition, it is depicted that the diameter of the interior channel 11 is not constant. In between the way from the distal to the proximal end a narrowing is present and as a result a smaller diameter is achieved. The different diameter, i.e. the larger diameter of the interior channel 11 and the smaller diameter at the narrowing, are depicted by arrows of different length. The narrowing or constriction within the interior channel 11 can be made from the same or a different material compared to the abutment 10.

The axes 12 and 22 are angled with respect to each other at an angle of ≥5 degrees. This angle is denoted α in FIG. 1.

The abutment 10 and the inlay 20 are at least partially fused to each other. Therefore, one could also describe the dental abutment system according to the invention as having an abutment section and an inlay section.

For better clarity the screw 30 is shown separately. It has a proximal end and a distal end, the distal end comprising a screw head 31 and the proximal end comprising a thread 32 for engaging with a bone implant.

The bottom-most drawing in FIG. 1 is a top view of a dental abutment system according to the invention, i.e. in view from a distal position downwards to a proximal position. The screw 30 cannot be seen, as will become apparent in later figures. In this top view the abutment 10, inlay 20 and interior channel 11 are depicted. The cross-sectional view of the abutment/inlay assembly is along the axis denoted "A". The portion of the interior channel 11 comprising a different, a smaller diameter is indicated by the section lining within the interior channel 11.

Figure 2A:
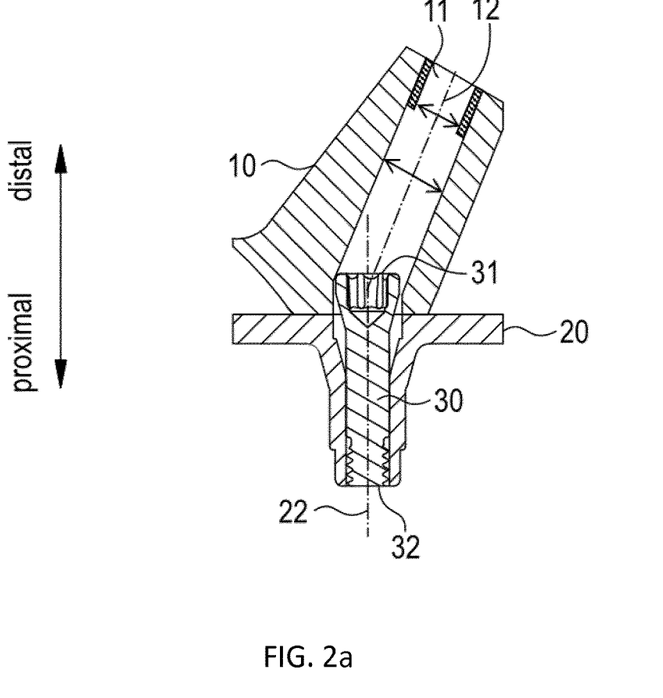
FIG. 2a shows a dental abutment system according to the invention in a first configuration

FIG. 2a shows a dental abutment system according to the invention in a first configuration. This configuration can be described as the configuration prior to fastening the system to an implant. The screw 30 at least partially occupies the interior channel 21 of the inlay 20. Here the screw has such a length that it extends out of the channel 21 in a distal direction.

With respect to dimensions of the channel 11 and the screw head 31, the maximum diameter of the interior channel 11 of the abutment 10 is ≤110% (preferably ≥80% to ≤105%) of the width of the screw head 31. This, together with the angle of the axes 12 and 22, it is possible that in an embodiment the screw 30 is a captive screw. In such configuration the screw cannot escape from inside the abutment system and also cannot be inserted into a fused assembly of abutment 10 and inlay 20. Nevertheless, it is also possible that the screw is inserted after forming the system. In addition, it is shown that the region of the interior channel 11 with a smaller diameter is now located at the distal end of the abutment 10.

Figure 2B:
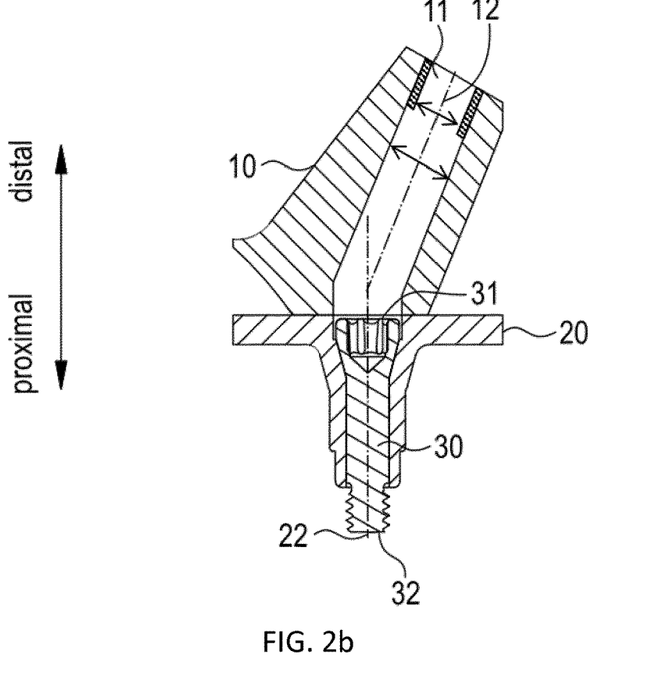
FIG. 2b shows a dental abutment system according to the invention in a second configuration

FIG. 2b shows a dental abutment system according to the invention in a second configuration. This configuration can be described as the configuration after fastening the system to an implant. The screw now extends out of the proximal end of the interior channel 21 (cf. FIG. 2a) of the inlay 20.

The thread 32 of screw 30 can now engage with a corresponding thread of a bone implant (not shown), therefore fastening the system to the implant.

In an embodiment of the system according to the invention the interior channel 11 of the abutment 10 comprises at least two different diameters and the ratio of the smallest and the largest diameter, calculated as diameter large divided by diameter small, is ≥1.05 and ≤2. Two diameters of the interior channel 11 mean, that the interior channel 11 does not comprise a single diameter. The two diameters are significantly different in the meaning, that small variations based on the manufacturing tolerances do not result in the formation of an interior channel 11 comprising different diameter. The interior channel 11 for instance comprises two different diameters in cases, wherein the interior channel 11 comprises different regions, wherein the diameter difference of the regions is at least 1 mm, preferably 2 and even more preferred 3 mm. A different diameter of the interior channel 11 at the contact zone between the abutment 10 and the inlay 10 alone does also not form an interior channel 11 comprising two different diameter. For instance, it is possible that the diameter regions in the interior channel 11 each extend for at least 1, preferably 2, more preferred 3 mm within the interior channel 11. It is further preferred, that the diameter ratio is ≥1.07 and ≤1.5, and especially preferred ≥1.1 and ≤1.25. Within the given diameter ranges the processing speed is increased, a substantial amount of material is saved, and the mechanical and structural properties of the overall implant are maintained.

In an embodiment of the system according to the invention the interior channel 11 of the abutment 10 comprises at least two different diameters and the diameter at the distal end is smaller than the diameter at the proximal end. It has been found useful that the diameter at the upper, i.e. distal, end of the device is smaller compared to vice versa configurations. In this case the interior channel 11 enlarges from the distal to the proximal end. This configuration keeps the accessible hole of the interior channel 11 rather small and mechanically protects the interior channel 11, but also allows for a significant reduction in processing time and material costs.

In a preferred embodiment of the system according to the invention the interior channel 11 of the abutment 10 comprises at least three different diameter regions, wherein the smallest diameter of the interior channel 11 is located in between two regions of the interior channel 11 comprising larger diameters. Such configuration, wherein the middle part of the interior channel 11 is smaller compared to the distal and proximal portion of the interior channel 11, has been found favorable, because the middle section of the interior channel 11 is stabilized and there is still enough space to insert and position the screw 31 in the interior channel 11. Furthermore, it has been found favorable, that the means for fixing the screw 31 are mechanically guided close to the bending region and this configuration may ease the overall assembling and fastening process.

In an embodiment of the system according to the invention the interior channel 11 of the abutment 10 comprises at least two regions of different diameter and the length ratio of the region comprising the smaller diameter and the region comprising the larger diameter, calculated as length of region with large divided by length of region with small diameter, is ≥0.1 and ≤4. It has been found useful, that a preferred length ratio within the interior channel 11 is maintained between the regions of different diameter. The length of a region is defined as the length of said region extending in the interior channel 11. Furthermore, if more than two regions are present the length of the different regions of the same diameter is summed up. Therefore, e.g. if three regions of different diameters are formed by a smaller diameter region in the middle of the interior channel 11, the length of the distal and proximal larger regions is summed up. If the overall length of the interior channel 11 is 15 mm and the upper and lower larger regions are each 5 mm in length and the smaller diameter region extents for 5 mm the ratio is calculated as ((5 mm+5 mm)/5 mm)=2. Within the above given ratio the mechanical stability of the device is maintained and a sufficient amount of material costs and processing time can be saved.

In another embodiment of the system according to the invention the interior channel 11 of the abutment 10 comprises at least two regions of different diameter and the symmetry axis of the different regions is displaced by ≥5% and ≤25% with respect to the smaller diameter. For handling and assembling it has been found useful that the symmetry axis of the different regions in the interior channel 11 are different. For instance, it is possible that the region of larger and smaller diameter each comprise the symmetry of a circle and the circle center of each (small and large) circle varies along the interior channel 11. Such configuration can, for instance, be achieved in cases, wherein one wall within the region of smaller diameter within the interior channel 11 is larger compared to the other wall. In this configuration the handling and assembling properties can be improved, because a screw driver or a similar assembling mean can be guided more efficiently compared to symmetric channel configurations. The overall displacement is given relative to the diameter of the region comprising a smaller diameter. If the diameter of the region comprising a smaller diameter comprises for instance a diameter of 10 mm, the displacement between the symmetry axes, i.e. the two circle centers, may be between 0.5 to 2.5 mm.

In an embodiment of the system according to the invention the inlay 20 is configured to mate with a bone implant. This enables a stronger connection of the abutment system to the implant.

In another embodiment of the system the maximum diameter of the interior channel 21 of the inlay 20 is ≤110% of the width of the screw thread 32. Preferably this diameter is ≤80% to ≥105%.

In another embodiment of the system the longitudinal axis 12 of the interior channel 11 of the abutment 10 and the longitudinal axis 22 of the interior channel 21 of the inlay 20 are angled with respect to each other at an angle of ≥20 degrees to ≤35 degrees. Such an angular range allows for the best accommodation of aesthetic and mechanical requirements, not the least accessibility of the screw to a screwing tool inserted into the channel. Preferably the angle is ≥22 degrees to ≤25 degrees.

In another embodiment of the system the abutment 10 is constructed from a first material, the inlay 20 is constructed from a second material and the screw 30 is constructed from a third material, the first, second and third material being the same or different from each other and independently selected from the group of metals, ceramics and polymers. It is preferred that at least the abutment 10 and the inlay 20 are manufactured from the same material.

In another embodiment of the system the abutment 10, the inlay 20 and/or the screw 30 are constructed from titanium, cobalt-chromium alloy, aluminum oxide, zirconium oxide or hydroxyl apatite. Titanium and CoCr alloy can be processed in selective laser sintering (SLS) or selective laser melting (SLM) or direct energy deposition (DED), e.g. laser cladding additive manufacturing techniques. Aluminum oxide, zirconium oxide and hydroxyl apatite can be processed in binder and/or material jetting additive manufacturing techniques.

In another embodiment of the system it comprises a plurality of abutments 10 and a common inlay formed by a plurality of connected inlays 20. Hence, not only individual tooth replacements but also entire bridges are encompassed in the present invention.

Figure 3:
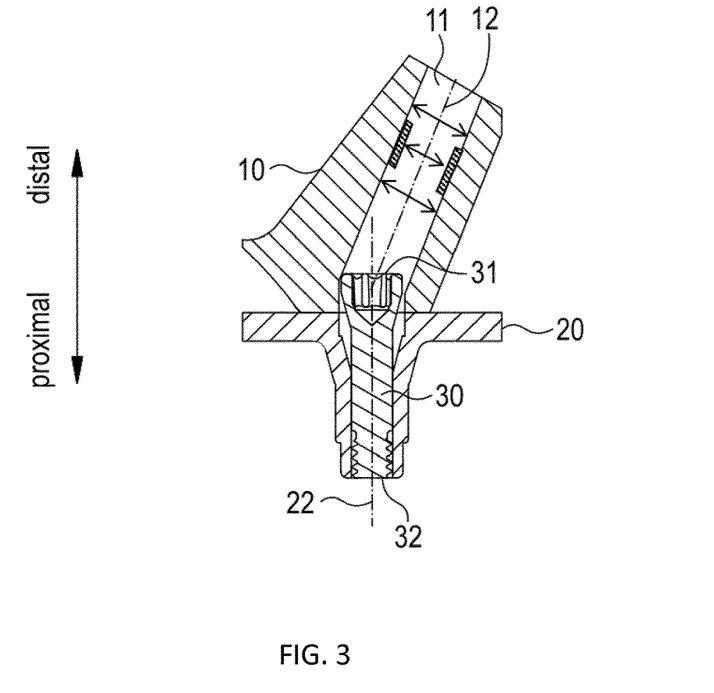
FIG. 3 shows a dental abutment system according to the invention in a third configuration

FIG. 3 exhibits a third configuration of the system according to the invention. In this figure the region comprising a smaller diameter of the interior channel 11 of the abutment 10 is located in between the distal and proximal end of the interior channel 11. The longitudinal extension of the region comprising a smaller diameter can vary and suitable length-scales can for instance be in between 1 and 10 mm. It can also be seen from this figure that the diameter at the distal end of the interior channel 11 and the diameter at the proximal end of the interior channel 11 is larger.

Figure 4:
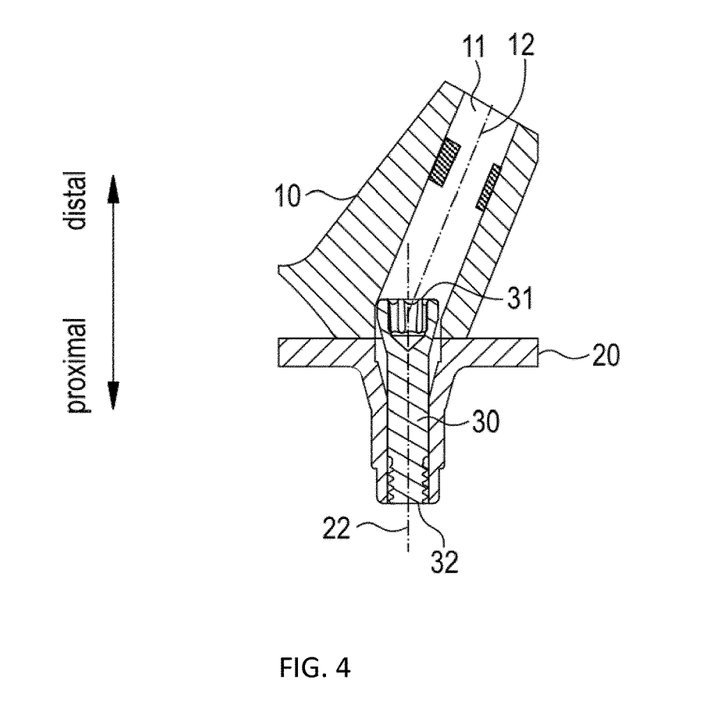
FIG. 4 shows a dental abutment system according to the invention in a fourth configuration

FIG. 4 shows a fourth configuration of the system according to the invention. In this figure the region comprising a smaller diameter of the interior channel 11 of the abutment 10 is located in between the distal and proximal end of the interior channel 11. It can also be seen from this figure that the diameter at the distal end of the interior channel 11 and the diameter at the proximal end of the interior channel 11 is larger. Furthermore, it is displayed that the symmetry axes of the region of the smaller diameter and the symmetry axis of the interior channel 11, i.e. the circle center as viewed from above, are not aligned but displaced.

Figure 5:
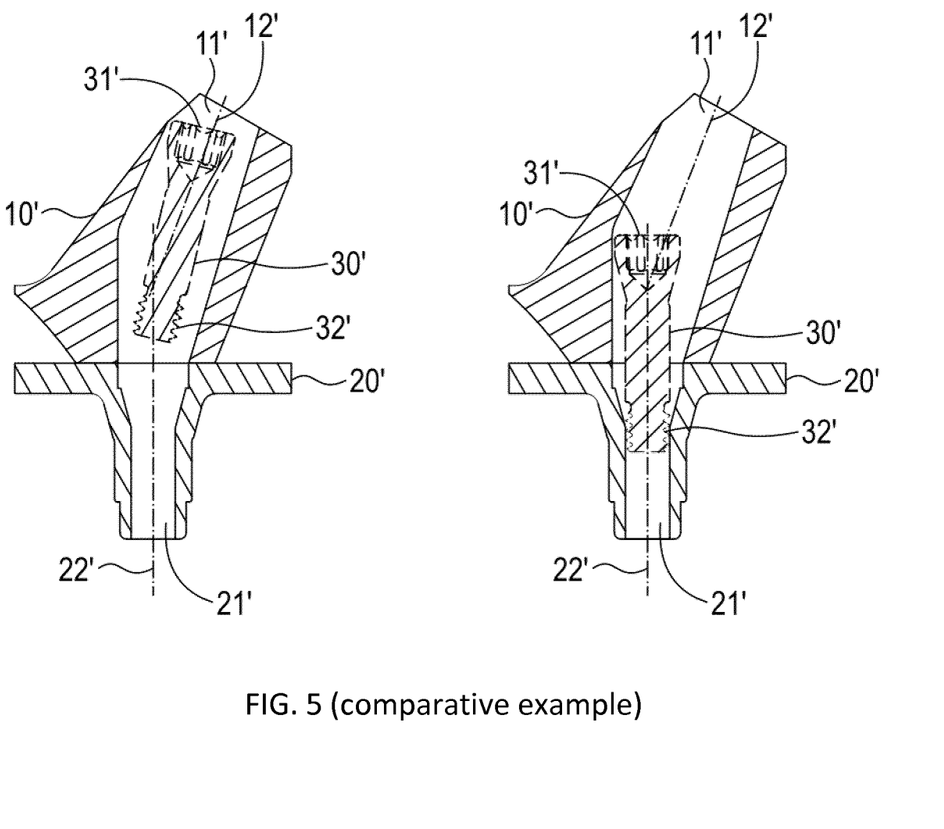
FIG. 5 shows a dental abutment system as a comparative example

FIG. 5 shows a dental abutment system as a comparative example. Depicted are abutments 10', inlays 20' and screws 30'. In analogy to FIG. 1 the systems have proximal and distal ends. As such, when implemented in the mandible of a patient, the proximal ends of the systems will face the jaw bone. In the systems depicted the abutments 10' located at the distal end and the inlay 20' at the proximal end.

The abutments 10' comprise interior channels 11' having a longitudinal axis 12' and the inlays 20' comprise an interior channel 21' having a longitudinal axis 22'. The screws 30' have a proximal end and a distal end, the distal end comprising a screw head 31' and the proximal end comprising a thread 32' for engaging with a bone implant.

Furthermore, the axes 12' and 22' are angled with respect to each other at an angle. The abutments 10' and the inlays 20' are fused to each other. As with the system according to the invention the abutments 10' and the inlays 20' are positioned relative to each other in such a way that the interior channels 11' of the abutments 10' extend into the interior channels 21' of the inlays 20'. Hence the channels have the same diameter at the interface of the abutments 10' and the inlays 20' and their cross-sections are superimposed upon each other.

In contrast to a preferred embodiment according to the invention the screws 30' are not captive screws. When installing the abutment system, a screw 30' will be passed through channel 11' and into channel 21'. As such the left-hand drawing of FIG. 5 may be seen as an early stage of screw insertion and the right-hand drawing as a later stage of screw insertion. It can be seen in the left-hand drawing that, because of the angle between the channels 11' and 22', the channel 11' needs to be much wider than in a system according to the invention. As wider channels necessitate more material removal when drilling the channel, the mechanical stability of at least the abutment 10' is lowered.

Figure 6:
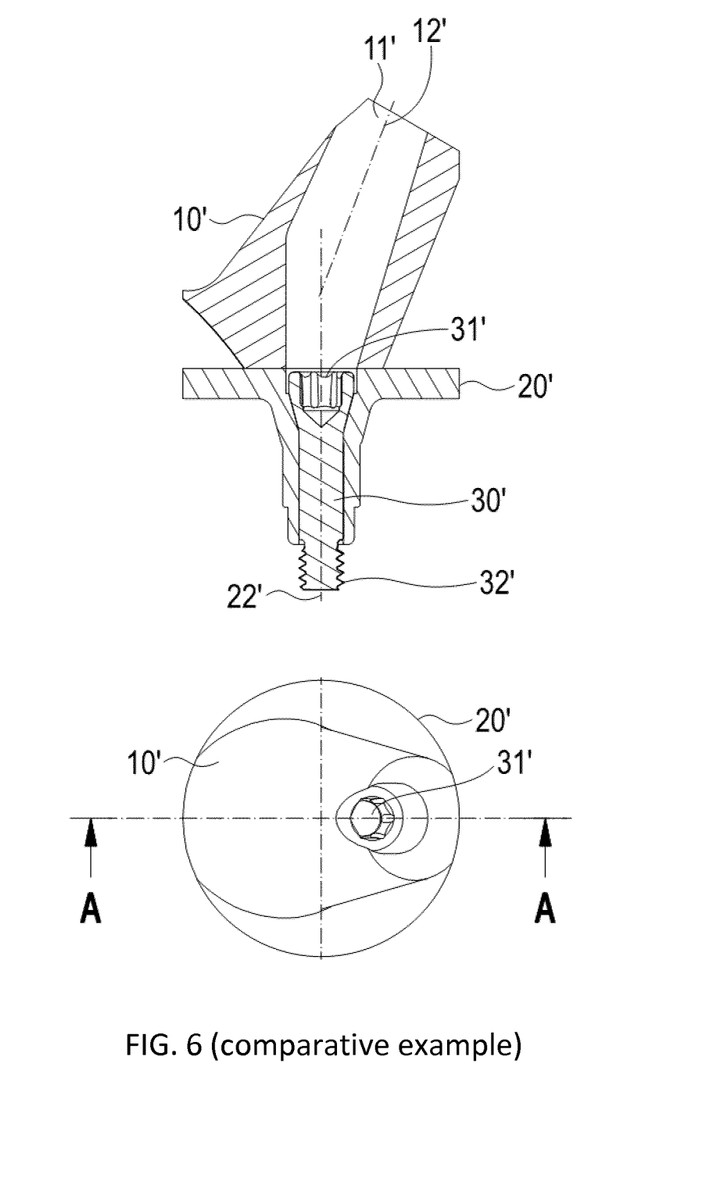
FIG. 6 shows a dental abutment system as a comparative example

FIG. 6 shows a final configuration of the comparative example depicted previously in FIG. 5. The thread 32' of screw 30' can now engage with a corresponding thread of a bone implant (not shown), therefore fastening the system to the implant.

The bottom-most drawing in FIG. 6 is a top view of the dental abutment system, i.e. in view from a distal position downwards to a proximal position. The screw head 31' can be seen as is apparent from the cross-sectional view along the axis denoted "A". In the top view the abutment 10' and inlay 20' are also depicted.

Figure 7:
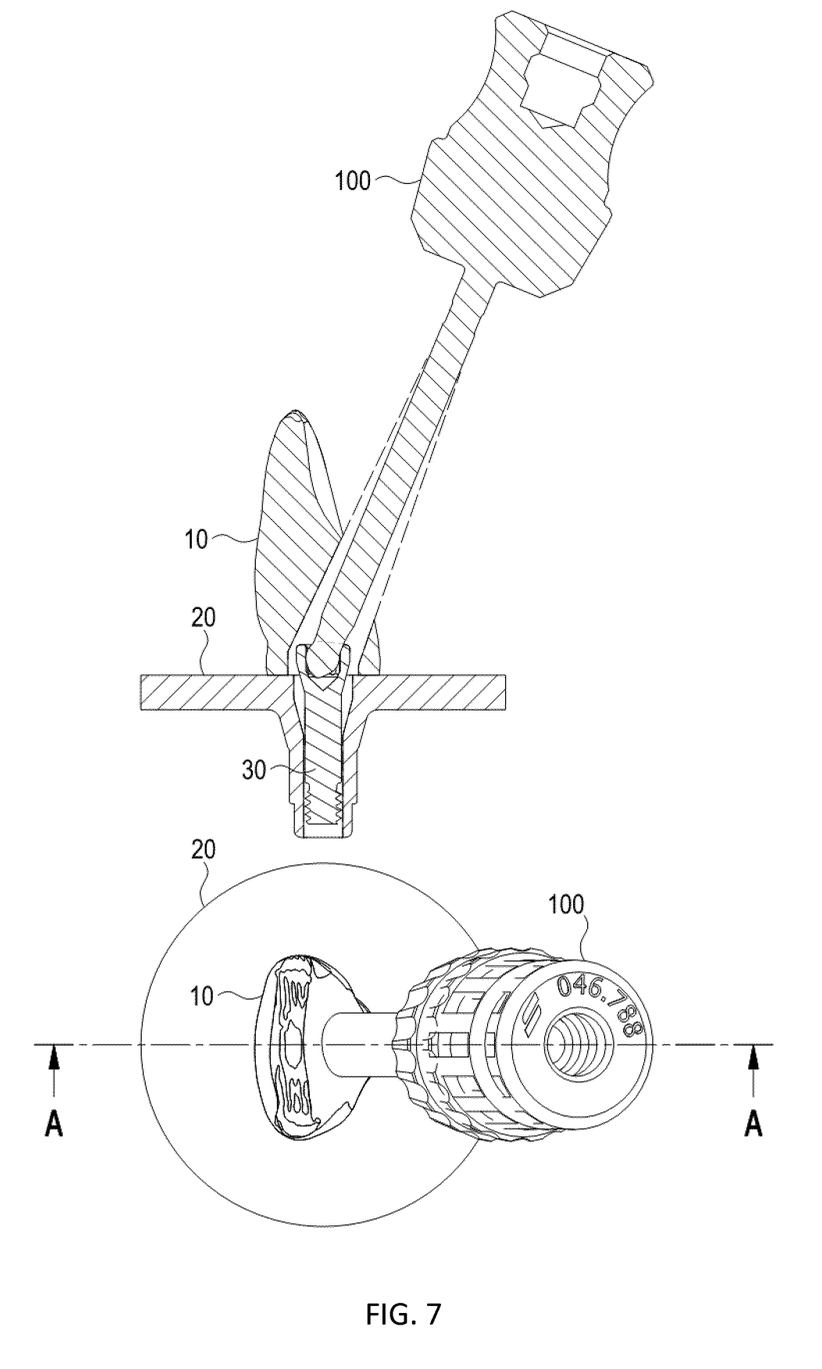
FIG. 7 shows a tool engaging with a dental abutment system according to the invention

FIG. 7 shows a tool 100 engaging with a dental abutment system according to the invention with an abutment 10, an inlay 20 and a screw 30. This arrangement can be encountered when the system is to be fastened to a bone implant. The tool 100 may be a round bolt hexagonal tool. Due to the round bolt of the tool it is possible to insert the tool into the head of the screw 30 at an angle for tightening the screw 30. The possible range of motion for the tool 100 is indicated by the dashed lines and their extension into the abutment 10.

The bottom-most drawing in FIG. 7 is a top view of the tool 100 and the dental abutment system, i.e. in view from a distal position downwards to a proximal position. The inserted tool 100, abutment 10 and inlay 20 can be seen as is apparent from the cross-sectional view along the axis denoted "A".

Figure 8:
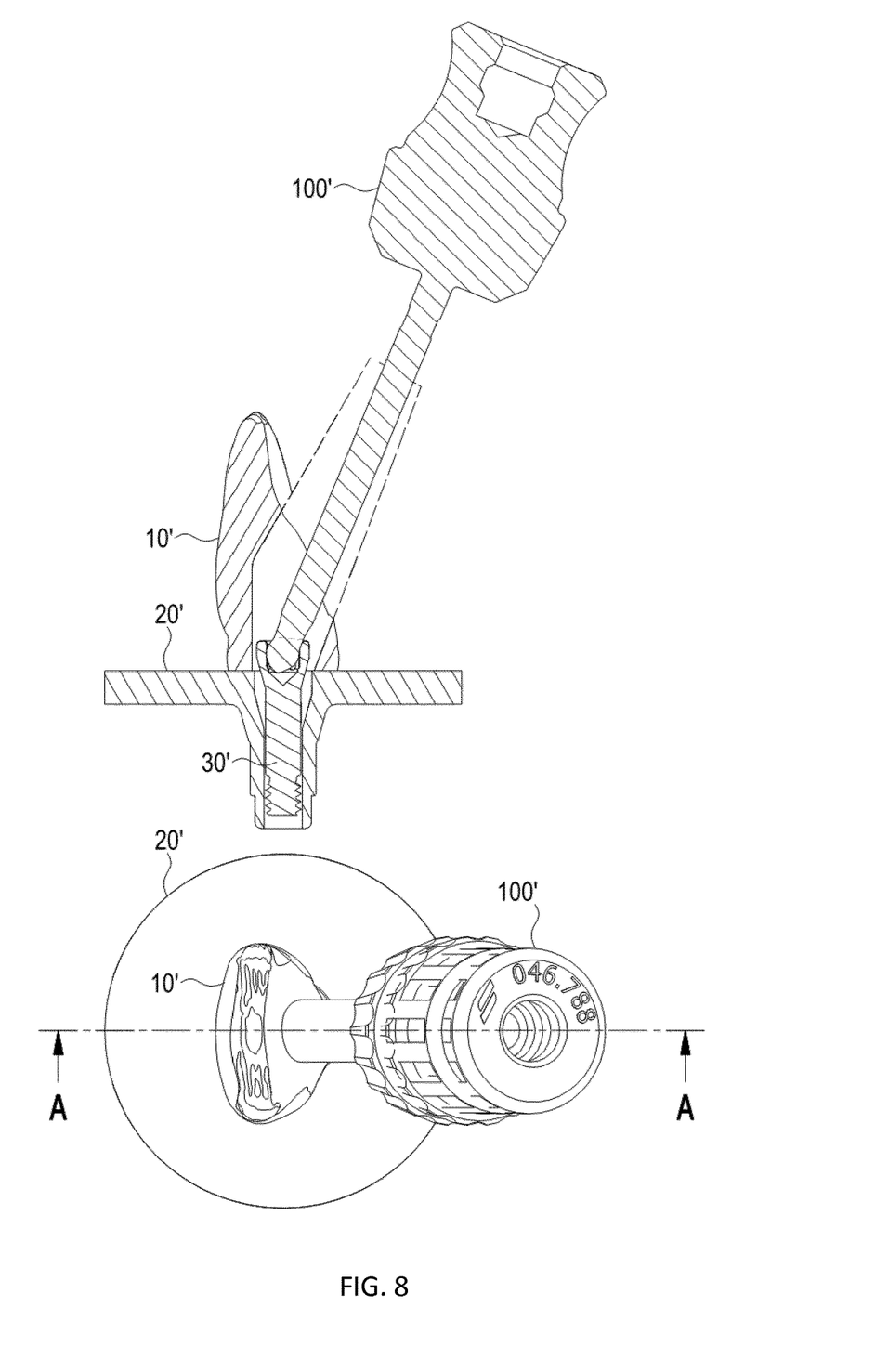
FIG. 8 shows a tool engaging with a dental abutment system as a comparative example

FIG. 8 shows a tool 100' engaging with a dental abutment system as a comparative example with an abutment 10', an inlay 20' and a screw 30'. This arrangement can also be encountered when the system is to be fastened to a bone implant. The tool 100' may also be a round bolt hexagonal tool. Due to the round bolt of the tool it is possible to insert the tool into the head of the screw 30' at an angle for tightening the screw 30'.

The possible range of motion for the tool 100' is indicated by the dashed lines and their extension into the abutment 10'. This range of motion may not strictly be necessary, but is due to the fact that the channel in the abutment 10' must be wide enough to permit insertion of the screw 30' around the bend before the screw 30' enters the inlay 20'. The material removal and therefore lower mechanical stability compared to the system according to the invention of FIG. 7 can readily be seen.

The bottom-most drawing in FIG. 8 is a top view of the tool 100' and the dental abutment system, i.e. in view from a distal position downwards to a proximal position. The inserted tool 100', abutment 10' and inlay 20' can be seen as is apparent from the cross-sectional view along the axis denoted "A".

LIST OF REFERENCE NUMERALS AND SIGNS

10, 10' abutment
11, 11' interior channel of abutment
12, 12' longitudinal axis of interior channel of abutment
20, 20' inlay
21, 21' interior channel of inlay
22, 22' longitudinal axis of interior channel of inlay
30, 30' screw
31, 31' screw head
32, 32' screw thread
100, 100' tool
$\alpha$ angle between axes 12 and 22

The invention claimed is:
1. A dental abutment system comprising:
an abutment including an interior channel having a longitudinal axis,
an inlay including an interior channel having a longitudinal axis, and
a screw that at least partially occupies the interior channel of the inlay, the screw including a proximal end and a distal end, the distal end comprising a screw head and the proximal end comprising a thread for engaging with a bone implant, wherein:

the system extends from a proximal end to a distal end, the abutment being at the distal end and the inlay at the proximal end of the system, the abutment and the inlay are positioned relative to each other in such a way that the interior channel of the abutment at least partially extends into the interior channel of the inlay, the abutment and the inlay are at least partially fused to each other, a diameter of the interior channel of the abutment varies from a distal end to a proximal end thereof and a smallest diameter is ≥102% and ≤110% of a width of the screw head, and the longitudinal axis of the interior channel of the abutment and the longitudinal axis of the interior channel of the inlay are angled with respect to each other at an angle of ≥5 degrees.

2. The system according to claim 1, wherein the interior channel of the abutment comprises at least two different diameters and a ratio of a largest diameter to the smallest diameter is ≥1.05 and ≤2.

3. The system according to claim 1, wherein the interior channel of the abutment comprises at least two different diameters and a diameter at the distal end is smaller than a diameter at the proximal end.

4. The system according to claim 1, wherein the interior channel of the abutment comprises at least three different diameters, wherein the smallest diameter of the interior channel is located in between two regions of the interior channel comprising larger diameters.

5. The system according to claim 1, wherein the interior channel of the abutment comprises at least two regions of different diameter and a length ratio of a length of a region comprising a larger diameter to a length of a region comprising a smaller diameter is ≥0.1 and ≤4.

6. The system according to claim 1, wherein the interior channel of the abutment comprises at least two regions of different diameter and a symmetry axis of the at least two regions of different diameter is displaced by ≥5% and ≤25% with respect to a smaller diameter.

7. The system according to claim 1, wherein the inlay is configured to mate with the bone implant.

8. The system according to claim 1, wherein a maximum diameter of the interior channel of the inlay is ≤110% of a width of the thread of the screw.

9. The system according to claim 1, wherein the longitudinal axis of the interior channel of the abutment and the longitudinal axis of the interior channel of the inlay are angled with respect to each other at an angle in a range of ≥20 degrees to ≤30 degrees.

10. The system according to claim 1, wherein:
the abutment is constructed from a first material,
the inlay is constructed from a second material,
the screw is constructed from a third material, and
the first, second and third materials are the same or different from each other and independently selected from the group of metals, ceramics and polymers.

11. The system according to claim 10, wherein the abutment, the inlay and/or the screw are constructed from titanium, cobalt-chromium alloy, aluminum oxide, zirconium oxide or hydroxyl apatite.

12. The system according to claim 1, comprising a plurality of abutments and a common inlay formed by a plurality of connected inlays.

13. A method of manufacturing the dental abutment system according to claim 1, comprising:
A) providing the inlay, the inlay including a proximal end and a distal end;
B) providing the screw or a partial screw comprising a partial screw head; and
C) forming the abutment at the distal end of the inlay using an additive manufacturing process, thereby at least partially fusing the formed abutment to the inlay.

14. The method according to claim 13, wherein the partial screw is provided in step B), and the screw is formed from the partial screw during the forming of the abutment in step C) by simultaneously finishing the partial screw head to form the screw head using the same additive manufacturing process for forming the abutment.

15. The method according to claim 13, wherein step A) and/or step B) are performed as an additive manufacturing step.

16. The method according to claim 13, wherein the additive manufacturing step or steps employ a metal powder, a ceramic powder or a polymer powder as their build material.

17. The method according to claim 13, wherein in step C) the abutment is formed according to spatial data of an individual person.

18. A non-transitory computer-readable medium comprising a plurality of control instructions, wherein the control instructions are configured to, when implemented in an additive manufacturing system, to cause the system to execute at least the step of:
forming an abutment at a distal end of an inlay using an additive manufacturing process,
the abutment comprising an interior channel having a longitudinal axis,
the inlay extending from a proximal end to the distal end and comprising an interior channel having a longitudinal axis,
the inlay comprises or is configured to comprise a screw, the screw extending from a proximal end to a distal end, the distal end of the screw comprising a screw head and the proximal end comprising a thread for engaging with a bone implant;
wherein:
the abutment and the inlay are positioned relative to each other in such a way that the interior channel of the abutment at least partially extends into the interior channel of the inlay;
the forming of the abutment is performed in such a manner that a diameter of the interior channel of the abutment varies from a distal end to a proximal end thereof and a smallest diameter of the interior channel of the abutment is ≥102% and ≤110% of a width of the screw head; and
the longitudinal axis of the interior channel of the abutment and the longitudinal axis of the interior channel of the inlay are angled with respect to each other at an angle of ≥5 degrees.

19. The non-transitory computer-readable medium according to claim 18, wherein the control instructions are further configured to cause the additive manufacturing system to execute, prior to the forming of the abutment, the step of:
simultaneously forming the inlay and the screw,
wherein:
the screw is at least partially located within the interior channel of the inlay, and the distal end of the screw is located at the distal end of the inlay.

20. The non-transitory computer-readable medium according to claim 18, comprising data for forming the abutment which correspond to spatial data of an individual person.

* * * * *